United States Patent [19]

Baker et al.

[11] 4,101,832
[45] Jul. 18, 1978

[54] MULTIPROBE EDDY CURRENT FLAW DETECTION DEVICE WITH MEANS TO RAISE AND LOWER THE INDIVIDUAL PROBES

[75] Inventors: Richard G. Baker, Cleveland Heights; Joseph P. Vild, Lyndhurst; Charles Griesfelder; Donald P. Fox, both of Cleveland, all of Ohio

[73] Assignee: Republic Steel Corporation, Cleveland, Ohio

[21] Appl. No.: 554,167

[22] Filed: Feb. 28, 1975

Related U.S. Application Data

[63] Continuation of Ser. No. 82,051, Oct. 19, 1970, abandoned.

[51] Int. Cl.² ............................................. G01R 33/12
[52] U.S. Cl. ...................................... 324/227; 324/238
[58] Field of Search .................................... 324/37, 40

[56] References Cited

U.S. PATENT DOCUMENTS

| | | | |
|---|---|---|---|
| 1,872,351 | 8/1932 | Schaake et al. | 324/37 |
| 1,933,547 | 11/1933 | Drake et al. | 324/37 |
| 2,124,579 | 7/1938 | Knerr et al. | 324/40 |
| 3,234,457 | 2/1966 | Soner et al. | 324/40 |
| 3,299,349 | 1/1967 | Tompkins et al. | 324/37 |
| 3,346,807 | 10/1967 | Wood et al. | 324/37 |
| 3,460,028 | 8/1969 | Beaver et al. | 324/37 |
| 3,568,049 | 3/1971 | Barton | 324/37 |

*Primary Examiner*—Robert J. Corcoran
*Attorney, Agent, or Firm*—Watts, Hoffman, Fisher & Heinke Co.

[57] ABSTRACT

A flaw detection device, and method of operation thereof, for inspecting an entire workpiece, such as a tube or pipe, for the presence of defects. The detection device includes a plurality of pickup arms mounted in spaced relation with respect to each other around a work path, and a plurality of sensing coils carried by each of the pickup arms. The pickup arms are each mounted on a support member to pivot on an axis transverse to the direction of the work path so that the sensing coils may be moved into proximity and around the circumference of a workpiece as the workpiece travels along the work path.

1 Claim, 8 Drawing Figures

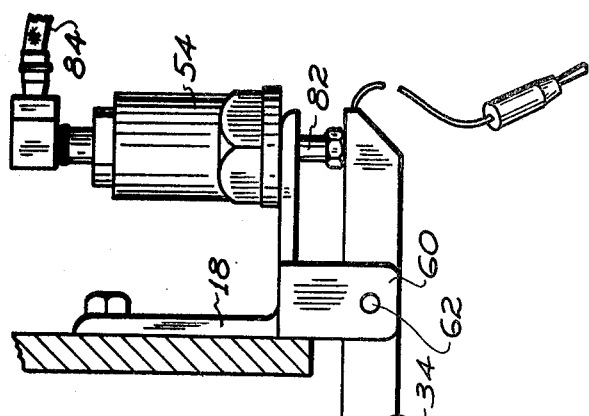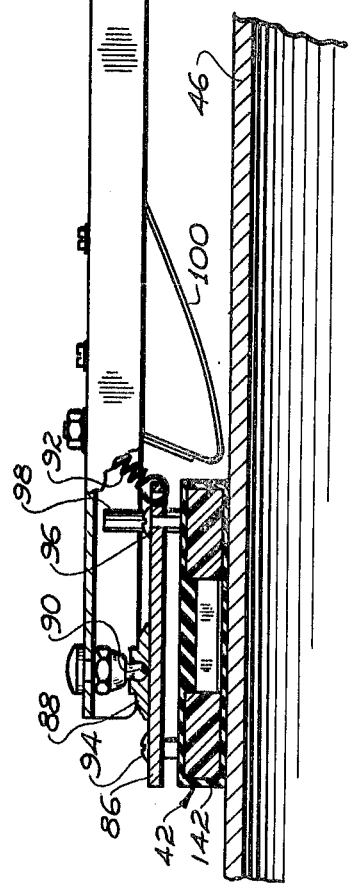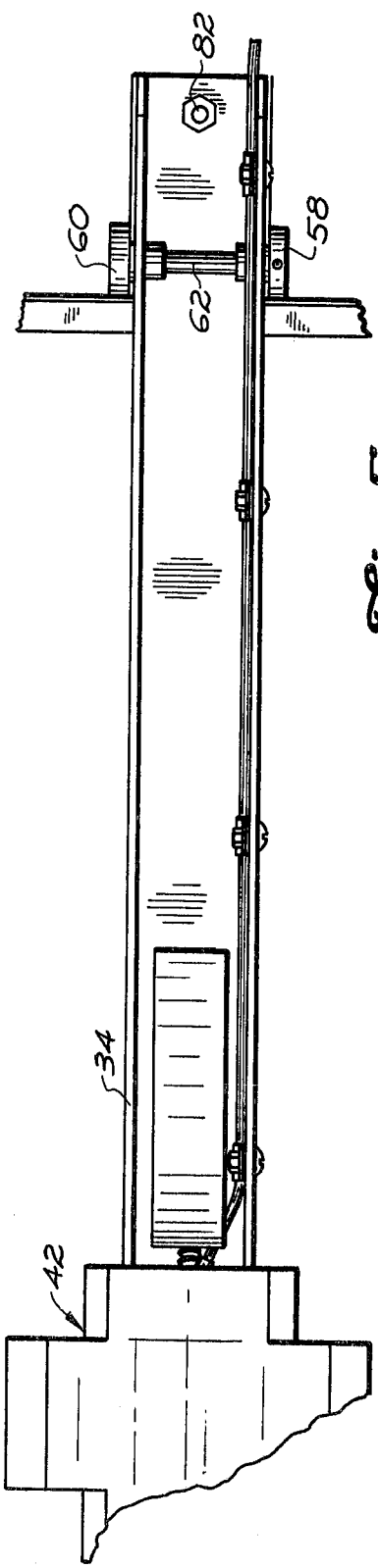

MULTIPROBE EDDY CURRENT FLAW DETECTION DEVICE WITH MEANS TO RAISE AND LOWER THE INDIVIDUAL PROBES

This is a continuation, of application Ser. No. 82,051, filed Oct. 19, 1970 now abandoned.

CROSS REFERENCE TO A RELATED PATENT

U.S. Pat. No. 3,234,457 to George W. Sower et al, entitled, "Non-Destructive Eddy Current Testing Device and Method Utilizing Sensing Means Movable Relative to the Excitation Means and Test Piece," issued on Feb. 8, 1966, and assigned to the same assignee as the present application.

BACKGROUND OF THE INVENTION

This invention pertains to a method and apparatus for testing articles for defects, and more particularly, to a flaw detection device for detecting the presence of defects in a workpiece as the workpiece travels along a work path.

The above-referenced U.S. Pat. No. 3,234,457 to George W. Sower et al, discloses a non-destructive eddy current testing device which utilizes a movable support arm for maintaining a sensing coil at a constant spaced relationship with respect to an object being tested. The movable arm is mounted for pivotal movement and is urged into a predetermined spaced relationship with respect to the object to be tested either by gravity, or through a suitable resilient biasing arrangement. Thus, as a workpiece, such as a pipe, moves along a path of travel, the sensing coil remains in a constant distance from the surface of the workpiece.

The eddy current testing device disclosed in the above-mentioned patent provides a very precise indication of a defect whenever the defect is passed in proximity to the sensing coil. An example of an application of that disclosed flaw detecting device is that of detecting the presence of a defect in a pipe weld or seam as the pipe travels along a work path.

It has been found, however, that in order to detect the presence of defects along a weld seam of a pipe by utilizing a single pickup arm and sensing coil, the weld seam must be constantly maintained in a generally circumferentially fixed position with respect to the sensing coil as the workpiece is moved along the work path. Alternatively, the sensing coil must be continuously positioned to maintain the coil in proximity to the seam. In order to maintain the position of the coil in a circumferentially fixed relationship to that of the seam, it has been necessary to utilize an automatic positioning control system for maintaining the coil in a proper position, or alternatively, to employ an operator to manually maintain the coil in a proper position with respect to the weld seam.

It has been found to be highly desirable to provide a flaw detection system for detecting defects from around the entire circumference of a workpiece as the workpiece travels along a work path thereby eliminating the requirement of continuously maintaining a sensing coil in a proper position with respect to a track, such as a weld seam, along the workpiece.

In addition, it has been found to be desirable to inspect an entire workpiece for the presence of defects, as opposed to the inspection of a single thin track along the workpiece.

One technique for inspecting an entire workpiece for the presence of defects is that of utilizing a single coil which is positioned to encircle the circumference of the workpiece. As the workpiece travels through the coil, the coil develops a signal representative of the value of all of the eddy currents which exist within the coil. In other words, the signal developed by the coil represents the average value of all of the eddy currents detected by the coil. With this type of arrangement, it is possible to detect large defects; however, frequently smaller defects remain undetected because of the signal averaging which inherently occurs in this type of system.

It is therefore an object of the present invention to provide a flaw detecting device for inspecting an entire workpiece or a predetermined portion of a workpiece for the presence of defects.

Another object of the present invention is to provide a flaw detecting device for detecting the presence of relatively small defects while inspecting a relatively large portion of a workpiece.

Another object of the present invention is to provide a flaw detection device for inspecting a relatively large portion of a workpiece, such as a pipe or tubing, which includes a plurality of sensing coils which may be moved into and out of proximity with the circumference of the workpiece.

Another object of the present invention is to provide a flaw detection device for inspecting a workpiece as the workpiece travels along a work path, and which provides an output indication representative of the position of a defect with respect to the circumference of the workpiece as well as with respect to the length of the workpiece.

Another object of the present invention is to provide a flaw detection device including a plurality of search coils each for inspecting a predetermined portion of a workpiece, as the workpiece travels a work path.

A still further object of the present invention is to provide a flaw detection device for inspecting an entire workpiece for the presence of defects, or a predetermined portion of the workpiece, which may be readily positioned around the circumference of the workpiece.

Another object of the present invention is to provide a sensing coil assembly for moving a plurality of sensing coils into and out of proximity with the circumference of a workpiece to be inspected.

A further object of the present invention is to provide an eddy current flaw detection system for simultaneously inspecting the entire surface of a workpiece, such as a pipe or tube, for the presence of defects.

SUMMARY OF THE INVENTION

The present invention is directed toward a flaw detection system, and method of operation thereof, thereby overcoming the noted disadvantages, and others, of such previous systems.

In accordance with one aspect of the present invention there is provided a flaw detection device for detecting defects in a workpiece as the workpiece travels along a work path. The detection device includes a plurality of support brackets mounted in spaced relation with respect to each other and to the workpiece, a plurality of pickup arms mounted on corresponding ones of the support brackets, and a plurality of sensing coils mounted on and supported by each of the pickup arms. An actuator device is coupled to each of the pickup arms for, upon actuation, moving the corresponding arm to position a corresponding sensing coil into and out of proximity with the workpiece.

In accordance with another aspect of the present invention, the support brackets each includes a pivot means having a pivotal axis in a plane extending in a direction perpendicular to the direction of the work path, and each of the pickup arms is mounted on a corresponding one of the pivot means so that the pickup arms may be pivoted in order to move the sensing coils into and out of proximity with the workpiece.

In accordance with another aspect of the present invention, the plurality of sensing coils are of a configuration and are mounted so as to completely encircle the workpiece.

In accordance with another aspect of the present invention, the sensing coils are of a configuration and are mounted so that when the coils are moved into proximity with the workpiece, the coils extend continuously around the entire circumference of the workpiece.

In accordance with another aspect of the present invention, the sensing coils are of a configuration and are mounted so that when the coils are moved into proximity with the workpiece, the coils overlap to form a closed loop around the circumference of the workpiece.

In accordance with another aspect of the present invention there is provided a method of detecting defects in a workpiece with a flaw detection device as the workpiece travels along a work path. The flaw detection device includes a plurality of pickup arms each carrying a sensing coil and each mounted for movement into and out of proximity with the workpiece. The method includes the steps of moving the plurality of pickup arms for positioning the sensing coils in proximity with the workpiece, inducing an eddy current into the workpiece, simultaneously moving the workpiece relative to each of the sensing coils, maintaining the plurality of sensing coils in substantially constant spaced relationship with the workpiece, detecting the induced eddy currents which exist at substantially every point along substantially an entire periphery of the workpiece with the sensing coils, and developing a plurality of electrical signals with the coils representative of the value of the detected eddy currents.

BRIEF DESCRIPTION OF DRAWINGS

FIGS. 2 through 6 are elevational views of the detection unit as illustrated in FIG. 1;

DESCRIPTION OF A PREFERRED EMBODIMENT

Figure 1:
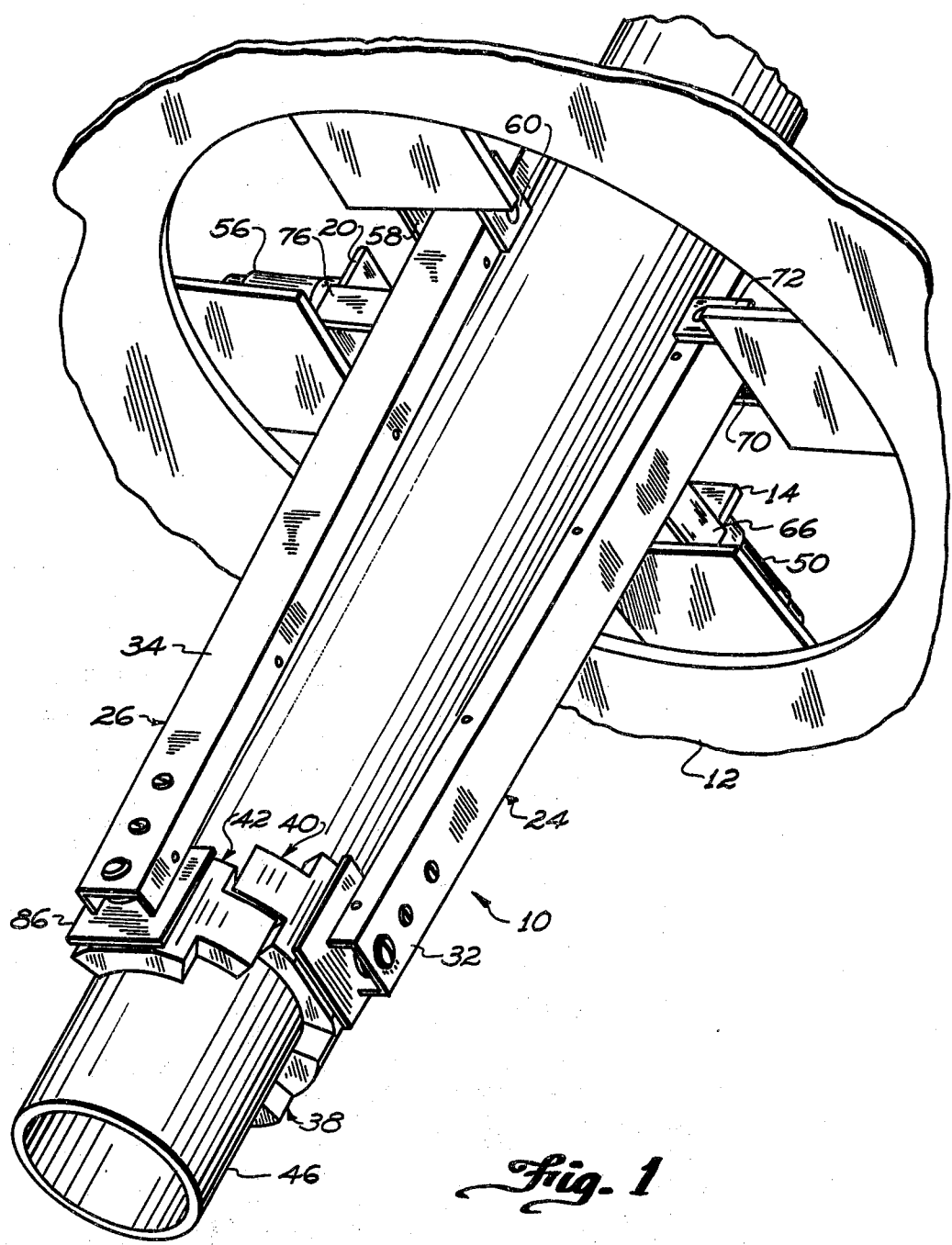
FIG. 1 is an oblique view of the detection unit of the present invention.

FIGS. 1 through 6 generally illustrate the detection unit 10 of the present invention which comprises a support frame 12, having four support brackets 14, 16, 18, 20 mounted therefor for supporting four sensing probes 22, 24, 26, 28. The sensing probes 22, 24, 26, 28 are generally comprised of four pickup arms 30, 32, 34, 36, each for carrying one of a plurality of sensing units 38, 40, 42, 44, respectively. The sensing units 38, 40, 42, 44 are positioned by the pickup arms 30, 32, 34, 36, respectively, in proximity with a workpiece 46, such as a pipe or tube, to be inspected as the workpiece travels along a work path.

Figure 3:
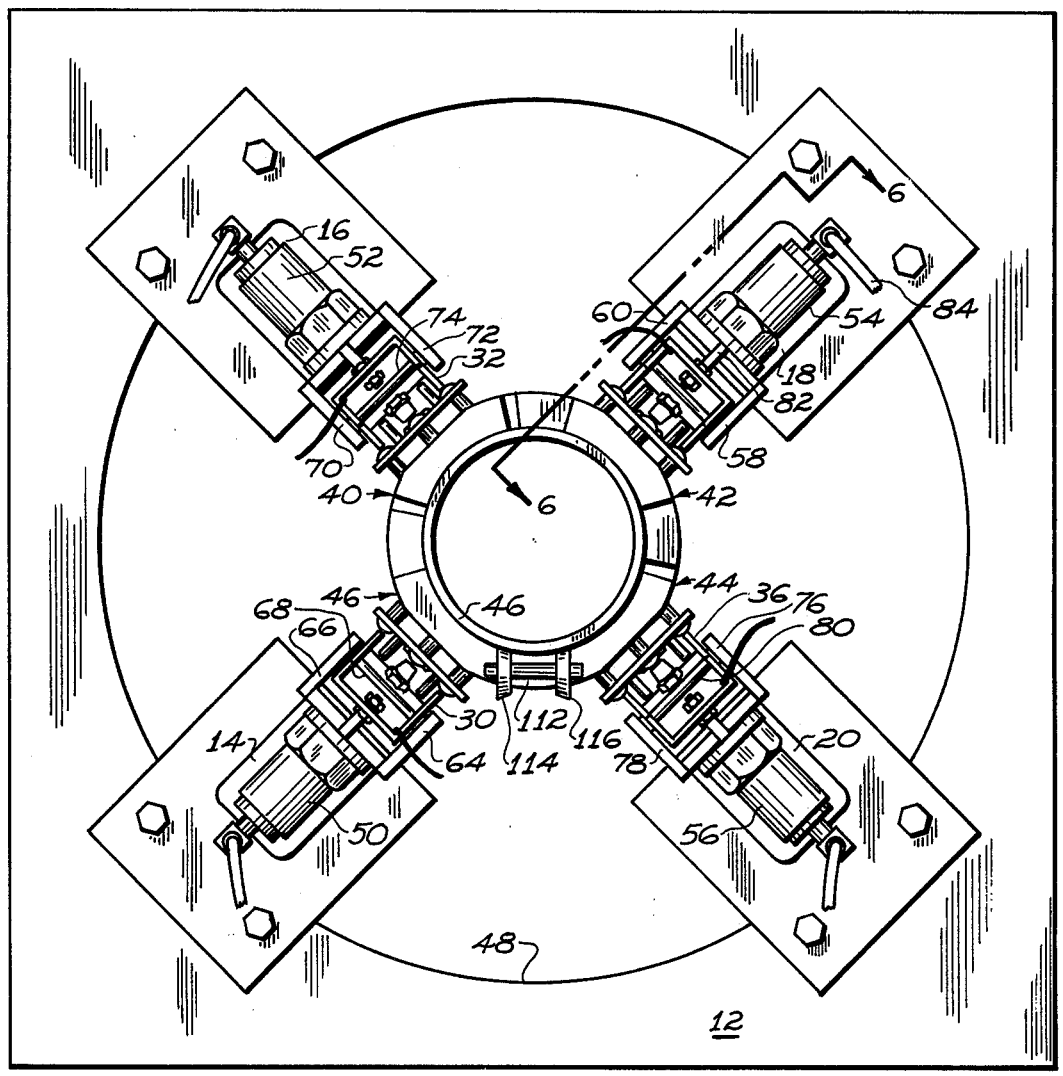

More particularly, and with reference to FIG. 3, the support frame 12 defines a through passage 48. The support brackets 14, 16, 18, 20 are mounted on the frame 12 and are positioned at equal distances around the passage 48, and are each of a generally L-shaped configuration in order to support one of a plurality of air cylinders 50, 52, 54, 56. The L-shaped support bracket 18 includes a pair of parallel extending flange portions 58, 60. A shaft 62 extends between the flange portions 58, 60 and is oriented so that its axis extends in a direction generally transverse to the direction of the work path of the workpiece 46. The pickup arm 34 is mounted on the shaft 62 for pivotal movement so that the end of the arm 34 which supports the sensing unit 42 may be moved toward or away from the workpiece 46 in order to move the sensing unit 42 into or out of proximity with the workpiece 46.

Similarly, the support bracket 14 includes a pair of flange portions 64, 66 for supporting a shaft 68. The shaft 68 has an axis which also extends in a direction transverse to the direction of the work path of the workpiece 46. In addition, the pickup arm 30 is pivotally mounted on the shaft 68 so that the end of the arm 30 which supports the sensing unit 38 may be moved toward or away from the workpiece 46 in order to move the sensing unit 38 into or out of proximity with the workpiece 46.

In a like manner, the support bracket 16 includes a pair of flange portions 70, 72. Extending between the flange portions 70, 72 is a shaft 74. The pickup arm 32 is pivotally mounted on the shaft 74 so that the sensing unit 40 which is carried by the pickup arm 32 may be moved into or out of proximity with the workpiece 40. The support bracket 20 includes a pair of flange portions 76, 78 for supporting a shaft 80. The pickup arm 36 is pivotally mounted on the shaft 80 so that the sensing unit 44 which is carried by the arm 36 may also be moved into and out of proximity with the workpiece 46. The shafts 74 and 80 are positioned so that the axes of these shafts extend in a direction transverse to the work path of the workpiece 46.

Figure 6:
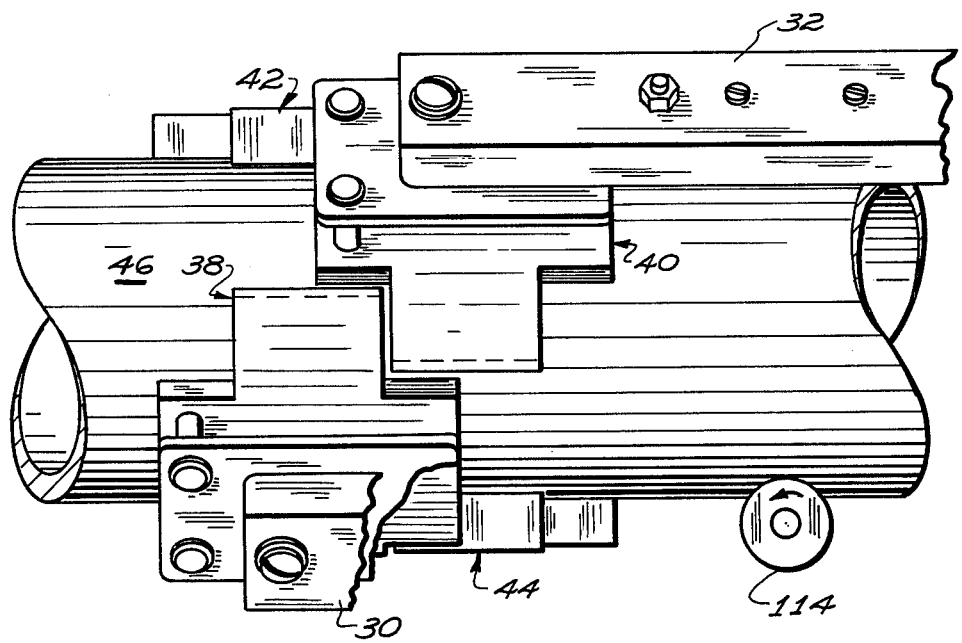

The air cylinders 50, 52, 54, 56 are respectively mounted on the L-shaped support brackets 14, 16, 18, 20. The air cylinder 54 includes a drive shaft 82 which is secured to the opposite end of pickup arm 34 from that end which carries the sensing unit 42. An inlet pipe 84 is coupled to the air cylinder 54 so that air pressure may be applied to the cylinder in order to move the drive shaft 82 downward, as viewed in FIG. 4, in order to pivot the pickup arm 34 in a generally clockwise direction about the shaft 62 in order to move the sensing unit 42 away from the workpiece 46. When the air pressure is removed from the inlet pipe 84, the shaft 82 is biased to return to the position as illustrated in FIG. 6 by a spring which is located within cylinder 54 in order to urge the sensing unit 42 against the surface of the workpiece 46.

Preferably, each of the pickup arms 30, 32, 34, 36, as well as the corresponding sensing units 38, 40, 42, 44, are similarly constructed, with the exception of the length of the pickup arms, therefore, a detailed description will be provided for only pickup arm 34 and its corresponding sensing unit 42, as is illustrated in FIGS. 4 and 5. More particularly, the pickup arm 32 is comprised of an elongated channel-shaped member for carrying a sensing unit mounting plate 86 having the sensing unit 42 mounted thereon. The mounting plate 86 is generally comprised of a flat plate having a socket member 88 mounted thereon for receiving a ball member 90 extending downward from the pickup arm 34 so as to form a ball and socket arrangement. A spring member 92 is attached between the arm 34 and the mounting plate 86 in order to slightly rotate the plate member in a counterclockwise direction as viewed in FIG. 4 when the arm 34 is in a retracted position, i.e., when the sensing unit is moved away from the workpiece 46.

The sensing unit 42 is of an arcuate configuration so as to be contoured to engage a portion of the circumference of a cylindrical workpiece. The sensing unit 42 is attached to the mounting plate 86 by four mounting screws of which only the two screws 94, 96 are illustrated in FIG. 4. A retainer pin 98 extends upward from the mounting plate 86 for preventing the travel of the mounting plate 86 past the point at which the pin 98 strikes the upper wall of the pickup arm 34.

A resilient biasing, or shield means member 100 extends downward from the pickup arm 34 for preventing the workpiece 46 from striking the right edge of the sensing unit 42 as the workpiece is initially inserted into the detection unit. When the pickup arm 34 is retracted, i.e., the sensing unit 42 is moved upward from the position shown in FIG. 4, the spring member 92 causes the mounting plate and sensing unit 42 to rotate in a generally counterclockwise direction so that the right edge of the sensing unit 42, as viewed in FIG. 4, is raised to a position above the lower edge of the resilient biasing member 100. With this arrangement, the workpiece 46 is prevented from striking the right edge of the sensing unit 42 as the workpiece is initially inserted into the detection unit 10.

When the pickup arm 34 is moved into the position as illustrated in FIG. 4, i.e., a position in which the sensing unit 42 is urged against the workpiece 46, the workpiece 46 bears against the left portion of the sensing unit 42 to thereby cause the sensing unit 42 to rotate slightly in a generally clockwise position so that the bottom surface of the sensing unit 42 engages the surface of the workpiece 46.

As illustrated in FIG. 5, an electrical cable extends from the sensing unit 42 and along the pickup arm 34 for providing an electrical connection between the sensing unit 42 and the detection circuitry.

Reference is now made to FIG. 6 which illustrates the overlapping configuration of the sensing units 38, 40, 42, 44 when the units are in proximity with the workpiece 46. More particularly, each of the sensing units are of the same configuration and include outwardly extending portions which interlock with the adjacent sensing units. The pickup arms 32, 36 are of a slightly shorter length than the arms 30, 34 to provide interlocking between adjacent sensing units. Thus, the sensing units 38, 40, 42, 44, when moved into proximity with the workpiece 46, provide a continuous ring around the workpiece 46.

As illustrated in FIGS. 3 and 6, a drive mechanism 112 including a pair of drive wheels 114, 116 engage the workpiece 46 in a direction to the left as viewed in FIG. 6 and along the work path.

Figure 7:
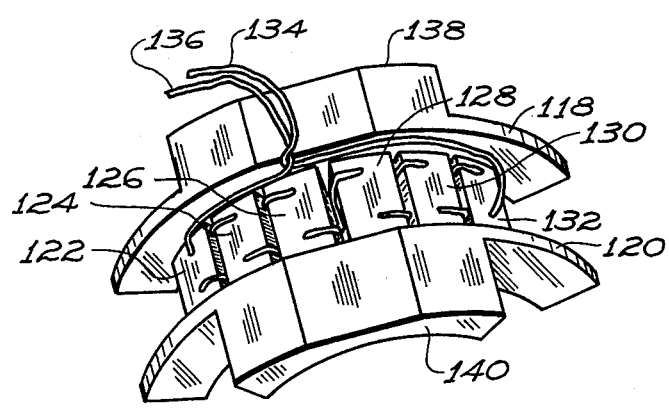
FIG. 7 is an oblique view illustrating the construction of a sensing unit as shown in FIG. 1; and, FIG. 8 is an electrical schematic, block diagram illustrating the electrical circuit of the present invention.

Reference is now made to FIG. 7 which illustrates in detail the construction of one of the sensing units 42. The other sensing units 38, 40, 44 are similarly constructed, therefore only sensing unit 42 will be described in detail. More particularly, sensing unit 42 includes a pair of thin arcuate members 118, 120, which are positioned generally parallel with respect to each other.

Extending between the arcuate shaped members 118, 120 are six sensing coils 122, 124, 126, 128, 130, 132 so as to form an arcuate configuration of the plurality of coils. The coils 122, 124, 126, 128, 130, 132 are series connected and the output terminals of these coils are connected to the output conductors 134, 136. Also, a pair of arcuate shaped support blocks 138, 140 are mounted on the arcuate members 118, 120, respectively, and extend outwardly for mounting the sensing unit 42 on the mounting plate 86. The arcuate members 118, 120 and the arcuate shape support blocks 138, 140 are formed of a plastic material and the entire assembly as illustrated in FIG. 7 is encapsulated with a thin insulative material 142, as illustrated in FIG. 4.

With reference to FIGS. 1 and 7, it is apparent that the coils 122, 124, 126, 128, 130, 132 of the sensing unit 42 extend for a distance so that when the sensing units 38, 40, 42, 44 are interlocked with each other, the sensing coils completely surround the circumference of the workpiece 46.

Figure 8:
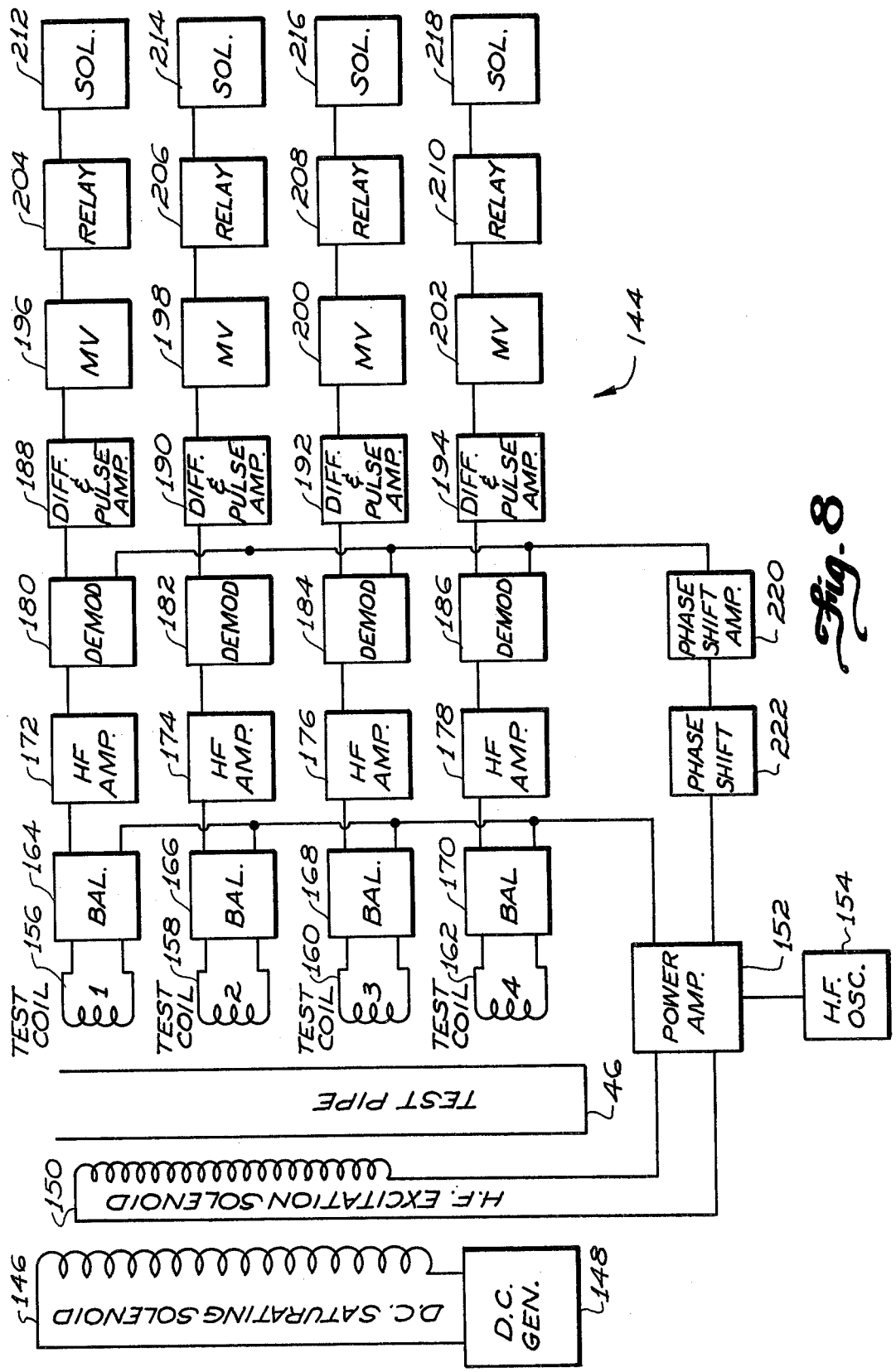

FIG. 8 generally illustrates the detection circuitry 144 which generally comprises a direct current saturating solenoid 146 which is energized by a direct current generator 148 and is positioned to induce a saturating magnetizing field into the workpiece 46. A high voltage excitation solenoid 150 is connected through a power amplifier 152 to a high frequency oscillator 154. The excitation solenoid 150 is positioned to induce eddy currents into the workpiece 46.

The sensing units 38, 40, 42, 44 respectively include the pickup coils 156, 158, 160, 162, each of which comprise six sensing coils, such as the sensing coils 122, 124, 126, 128, 130, 132 of the sensing unit 42.

The terminals of the pickup coils 156, 158, 160, 162 are connected to suitable balancing networks 164, 166, 168, 170, respectively, each of which may take the form of a Wheatstone bridge circuit. The output terminals of the balancing networks 164, 166, 168, 170 are respectively connected through the high frequency amplifiers 172, 174, 176, 178 to the demodulator circuits 180, 182, 184, 186, respectively. Also, the output terminals of the demodulator circuits 180, 182, 184, 186 are respectively connected through the differential and pulse amplifiers 188, 190, 192, 194, the multivibrator circuits 196, 198, 200, 202, respectively, the relay circuits 204, 206, 208, 210, respectively to the solenoid circuits 212, 214, 216, 218, respectively.

The output terminals of the demodulator circuits 180, 182, 184, 186 are also connected through a phase shift amplifier 220 and a phase shift circuit 222 to the power amplifier 152, which is in turn coupled to the balancing networks 164, 166, 168, 170.

Thus, each of the pickup coils 156, 158, 160, 162 monitors a predetermined segment of the circumference of the workpiece as the workpiece passes along the work path and the signals developed by the solenoids 212, 214, 216, 218 are indicative not only of the presence of a defect, but also the segment of the circumference of the workpiece 46 on which the defect appears.

Figure 2:
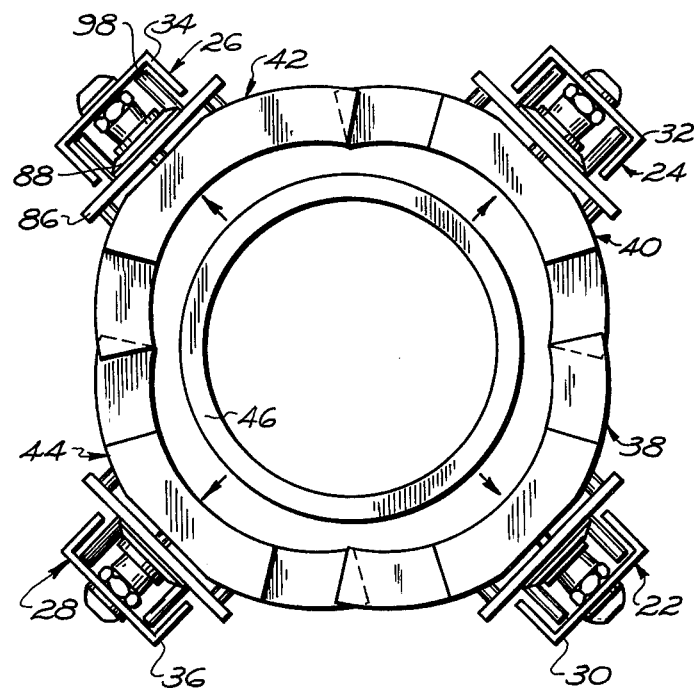

Thus, in operation, the air cylinders 50, 52, 54, 56 may be actuated to move the pickup arms 30, 32, 34, 36 so that the sensing units 38, 40, 42, 44 are moved to a retracted position as illustrated in FIG. 2. A workpiece, such as the tube or pipe 46, may then be inserted through the passageway 48 of the support frame 12 and through the ring of sensing units 38, 40, 42, 44 to a position as shown in FIG. 1. The air cylinders 50, 52, 54, 56 may then be actuated to a second position in which the sensing units 38, 40, 42, 44 are moved into proximity with the workpiece 46 as illustrated in FIGS. 1 and 3. The workpiece 46 is then driven along the work path by the drive mechanism 112.

As the workpiece 46 moves along the work path, the sensing coils of the sensing units 38, 40, 42, 44 are positioned around the entire circumference of the workpiece 46 so that defects which are located at any point on the workpiece are detected by the sensing coils.

The signals developed by the sensing coils at each of the sensing units 38, 40, 42, 44 are respectively applied to one of the four channels as defined by the balancing networks 164, 166, 168, 170 to provide an output indication at the respective one of the solenoids 212, 214, 216, 218 thereby indicating the presence of a defect as well as the portion of the circumference at which the defect is located.

Although the invention has been described in its preferred form, it is to be understood that the present disclosure of the preferred form has been made only by way of an example and that numerous changes in the details of construction and the combination and arrangement of parts may be resorted to without departing from the spirit and scope of the invention as hereinafter claimed.

Having thus described our invention, we claim:

1. In an eddy current flaw detection device for detecting defects in a workpiece as the workpiece travels along a work path;
   (a) energizing means for causing a current to circulate in the workpiece in an inspection station along the path;
   (b) a plurality of pickup arms each pivotally mounted for movement toward and away from the path between inspection and storage positions;
   (c) a plurality of sets of individual sensing coils with each set of coils mounted on and supported by a corresponding and different one of said pickup arms;
   (d) said sets of sensing coils substantially completely surround a circumference of a workpiece when the sets of sensing coils are in proximity with the workpiece and the arms are moved in their sensing positions;
   (e) the individual sensing coils in each set being rigidly secured in spaced relationship with respect to each other for sensing changes in the current over a circumferential area of the workpiece;
   (f) a plurality of actuators respectively coupled to a corresponding one of said plurality of pickup arms for moving the respective pickup arms to their storage positions for maintaining the sensing coils out of proximity with the workpiece path and to move the arms to their inspection positions for maintaining the sensing coils in proximity with the workpiece;
   (g) each of the sets having an edge which is a leading edge with respect to the direction of workpiece travel along the path;
   (h) resilient shield means projecting in front of the leading edge of at least one set;
   (i) spring means for urging the at least one set away from the path until the shield means is between said leading edge and the path to protect the sensing set from collision with a workpiece advancing along the path into the station;
   (j) a plurality of bridge circuit means coupled to a respective set of sensing coils, each bridge circuit means having an input circuit coupled to the corresponding set of sensing coils and an output circuit for developing a control signal having a value representative of a level of unbalance on the corresponding set of sensing coils; and,
   (k) a like plurality of indicator circuit means each of which are coupled to the output circuit of a corresponding bridge circuit means for receiving the value of said control signal and developing an output signal indicative of both the occurrence and location of a flaw in the workpiece when the value of the control signal exceeds a predetermined value.

* * * * *